United States Patent
Akazawa et al.

(10) Patent No.: US 8,987,674 B2
(45) Date of Patent: Mar. 24, 2015

(54) DATA PROCESSING METHOD FOR NUCLEAR MEDICINE, AND A NUCLEAR MEDICINE DIAGNOSTIC APPARATUS

(75) Inventors: Ayako Akazawa, Kyoto (JP); Keishi Kitamura, Kyoto (JP); Yoshihiro Yamada, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 211 days.

(21) Appl. No.: 13/388,792

(22) PCT Filed: Sep. 4, 2009

(86) PCT No.: PCT/JP2009/004381
§ 371 (c)(1),
(2), (4) Date: Feb. 3, 2012

(87) PCT Pub. No.: WO2011/027402
PCT Pub. Date: Mar. 10, 2011

(65) Prior Publication Data
US 2012/0126125 A1    May 24, 2012

(51) Int. Cl.
*G01T 1/166*    (2006.01)
*G01T 1/29*    (2006.01)

(52) U.S. Cl.
CPC ................... *G01T 1/2985* (2013.01)
USPC .................................. 250/363.04

(58) Field of Classification Search
USPC .................................. 250/363.04
See application file for complete search history.

(56) References Cited

U.S. PATENT DOCUMENTS

| | | | | |
|---|---|---|---|---|
| 5,224,037 | A * | 6/1993 | Jones et al. | 382/131 |
| 7,456,406 | B2 * | 11/2008 | Cho et al. | 250/363.04 |
| 2007/0075249 | A1 * | 4/2007 | Wang et al. | 250/363.04 |
| 2007/0153972 | A1 * | 7/2007 | Fujishige et al. | 378/19 |
| 2007/0201611 | A1 * | 8/2007 | Pratx et al. | 378/4 |
| 2007/0278410 | A1 * | 12/2007 | Cho et al. | 250/363.03 |
| 2008/0217540 | A1 * | 9/2008 | Panin et al. | 250/363.03 |
| 2009/0123048 | A1 * | 5/2009 | Leroux et al. | 382/131 |
| 2010/0057819 | A1 * | 3/2010 | Panin | 708/203 |
| 2010/0074500 | A1 * | 3/2010 | Defrise et al. | 382/131 |
| 2010/0272335 | A1 * | 10/2010 | Hu et al. | 382/131 |
| 2012/0070050 | A1 * | 3/2012 | Panin | 382/131 |

OTHER PUBLICATIONS

Fukano, Atsushi et al., "Performance Evaluation of Relaxed Block-Iterative Algorithms for 3-D PET Reconstruction", IEEE Transactions on Nuclear Science, 2004, vol. 5, pp. 2830-2834.
(Continued)

*Primary Examiner* — David J Makiya
*Assistant Examiner* — Taeho Jo
(74) *Attorney, Agent, or Firm* — Cheng Law Group, PLLC

(57) ABSTRACT

A PET apparatus and a processing method according in this invention carry out arithmetic processes in parallel, in steps S4 (forward projection) and S5 (back projection), for every LOR, on list data (created from event data obtained by detecting gamma rays), and can therefore be applied to other arithmetic mechanisms and have versatility. Since parallel processing is carried out on the list data and the parallel processing is carried out in each of steps S4 (forward projection) and S5 (back projection), a competition for memory can be prevented to realize an improvement in speed. As a result, high versatility and an improvement in speed of the calculations can be attained.

7 Claims, 6 Drawing Sheets

(56) References Cited

OTHER PUBLICATIONS

Tanaka, Eiichi, "Present Situation and Prospect of the Method of Reconstructing PET Images", Japanese Society of Radiological Technology Magazine, Hamamatsu Photonics Kabushiki Kaisha, 2006, vol. 62, No. 6, pp. 771-777.

Yang, Haiquan et al., "Accelerating Backprojections via CUDA Architecture", 9th International Meeting on Fully Three-Dimensional Image Reconstruction in Radiology and Nuclear Medicine, Lindau, Germany, Jul. 2007, pp. 52-55.

Pratx, Guiliem et al., "Fast, Accurate and Shift-Varying Line Projections for Iterative Reconstruction Using the GPU", IEEE Transactions on Medical Imaging, 2009, vol. 28, No. 3, pp. 435-445.

* cited by examiner

US 8,987,674 B2

DATA PROCESSING METHOD FOR NUCLEAR MEDICINE, AND A NUCLEAR MEDICINE DIAGNOSTIC APPARATUS

This application is a National Stage Application of International Application No. PCT/JP2009/004381, filed Sep. 4, 2009.

TECHNICAL FIELD

This invention relates to a data processing method for nuclear medicine and a nuclear medicine diagnostic apparatus which perform forward projection calculations and back projection calculations of list data created from event data obtained by detecting radiation.

BACKGROUND ART

A PET (Positron Emission Tomography) apparatus will be described as an example of the above nuclear medicine diagnostic apparatus, i.e. ECT (Emission Computed Tomography) apparatus. A PET apparatus is constructed to detect a plurality of photons generated by annihilation of positrons, and reconstruct a sectional image of a subject only when a plurality of detectors detect gamma rays at the same time (that is, only when coincidences are counted).

With this PET apparatus, quantitative measurement of various bodily functions can be made by serially measuring a process of drug concentration in tissues of interest after medicating the subject with a radioactive drug. Therefore, images obtained by the PET apparatus have functional information.

Specifically, to describe this by taking the human body as an example of the subject, a positron-emitting isotope (e.g. $^{15}$O, $^{18}$F, $^{11}$C or the like) is injected into the body of the subject, and gamma rays generating when the positrons released therefrom combine with electrons are detected. This detection of the gamma rays is carried out by a detector array consisting of numerous gamma-ray detectors arranged in a ring form circling around the body axis which is the longitudinal axis of the subject. And these are determined within a plane with a computer calculating by the same technique as usual X-ray CT (Computed Tomography), and an image of the subject is created.

Iterative approximation methods (see Nonpatent Document 1, for example) such as ML-EM (Maximum Likelihood Expectation Maximization), OSEM (Ordered Subset Expectation Maximization), RAMLA (Row-Action Maximum Likelihood Algorithm) and DRAMA (Dynamic Row-Action Maximum Likelihood Algorithm) are an indispensable technique for reconstructing images in nuclear medicine diagnostic apparatus like PET apparatus.

An occurrence of detecting gamma rays is called "event". Data of coincidences counted is called "coincidence data". Data not counted as coincidences is called "single event data". Data for every event transmitted from the gantry of the PET apparatus is called "list data". This list data has position information such as X-coordinate, Y-coordinate and Z-coordinate, time information and so on for every event, and such information is arranged in a time series.

On the other hand, this list data is converted into a histogram by carrying out histogram processing which integrates the list data based on time, to acquire histogram data. This histogram data is data integrated in a predetermined time. As this histogram data, there are sinograms in which the vertical axis represents directions of projection, and the horizontal axis represents pixels.

In recent years, an iterative approximation using this list data has also been performed (see Nonpatent Document 2, for example). However, in the case of a mode using list data (which is called "list mode"), data increases by an amount corresponding to the number of events, and its problem lies in the large amount of calculation. The iterative approximation using this list data involves a still larger amount of calculation.

So, a need for parallel calculations arises with the list mode. The parallel calculations carried out in many cases until now are MIMD (Multiple Instruction Multiple Data) type calculations such as MPI (Message Passing Interface). In the MIMD (Multiple Instruction Multiple Data) type calculations, a plurality of processors carry out parallel processes of a plurality of different data, which not only requires much memory area, but also requires numerous processors.

In recent years, on the other hand, research has been conducted on parallelization of forward projection processes and back projection processes which can also be said the core of image reconstruction, as parallel calculations of an iterative approximation using a GPU (Graphics Processing Unit) (see Nonpatent Document 3, for example). The parallel calculations using a GPU are classified under SIMD (Single Instruction Multiple Data) type calculations.

The SIMD (Single Instruction Multiple Data) type calculations can simultaneously process a plurality of data on one command, and are therefore suited for a process that performs the same arithmetic process for a large amount of calculation. However, when carrying out parallel calculations of the forward projection process and back projection process using the GPU, writing to the same memory (what is called "competition for memory") may occur, and therefore a contrivance is needed for parallelization.

Nonpatent Document 3 uses sinograms, and Nonpatent Document 4 uses list data.

[Nonpatent Document 1]
Eiichi Tanaka, "Present Situation and Prospect of the Method of Reconstructing PET Images", the Japanese Society of Radiological Technology magazine, Hamamatsu Photonics Kabushiki Kaisha, Vol. 62, No. 6, 771-777, (2006).

[Nonpatent Document 2]
A. Fukano, F. Nakayama, H. Kudo, "Performance evaluation of relaxed block-iterative algorithms for 3-D PET reconstruction," IEEE Trans. Nucl. Sci., Vol. 5, pp. 2830-2834, 2004.

[Nonpatent Document 3]
H. Yang, M. Li, K. Koizumi, and H. Kudo, "Accelerating backprojections via CUDA architecture," in Proceedings of the 9th International Meeting on Fully Three-Dimensional Image Reconstruction in Radiology and Nuclear Medicine, pp. 52-55, Lindau, Germany, July 2007.

[Nonpatent Document 4]
Guillem Pratx, Craig S. Levin et al, "Fast, Accurate and Shift-Varying Line Projections for Iterative Reconstruction Using the GPU", IEEE Trans. Med. Imaging., Vol. 28, No 3, pp. 435-445, 2009.

DISCLOSURE OF THE INVENTION

Problem to be Solved by the Invention

However, the technique reported in Nonpatent Document 4 noted above uses the mechanism peculiar to the GPU, and has a problem that application to SIMD type mechanisms other than the GPU is difficult. The GPU has primarily been intended for image processing, and use of the mechanism peculiar to the GPU refers to using a pixel shader or a vertex shader, after handling data as a texture image.

This invention has been made having regard to the state of the art noted above, and its object is to provide a data processing method for nuclear medicine and a nuclear medicine diagnostic apparatus which are highly versatile and can attain an improvement in the speed of calculations.

Means for Solving the Problem

To fulfill the above object, this invention provides the following construction.

A data processing method for nuclear medicine according to this invention comprises a forward projection processing step for obtaining forward projection processed data by carrying out, in parallel for every LOR, forward projection calculations of list data created from event data obtained by detecting radiation; and a back projection processing step for carrying out back projection calculations of the forward projection processed data or the list data in parallel for every area divided from sections of image space.

According to the data processing method for nuclear medicine of this invention, the forward projection processing step obtains forward projection processed data by carrying out, in parallel for every LOR (Line Of Response), forward projection calculations of the list data created from the event data obtained by detecting radiation. The back projection processing step carries out back projection calculations of the forward projection processed data or the list data in parallel for every area divided from sections of the image space. Since the arithmetic process is carried out in parallel on the list data for every LOR, the forward projection calculations and back projection calculations can be realized without using the mechanism peculiar to the GPU, for example, which can be applied to other arithmetic mechanisms and have versatility. Since parallel processing is carried out on the list data and the parallel processing is carried out through the forward projection calculations and back projection calculations, respectively, a competition for memory can be prevented to realize an improvement in speed. In the back projection calculations, as distinct from the forward projection calculations, a competition for memory may take place. In order to prevent this, the back projection processing step carries out the back projection calculations in parallel for every area divided from sections of the image space. As a result, high versatility and an improvement in the speed of calculations can be attained.

Since main directions of the LORs are located at random, it is preferable to classify the main directions first. That is, in the data processing method for nuclear medicine of this invention, it is preferred that a main direction determining step determines a main direction of the LOR based on a vector of the LOR and a direction of arrangement of detectors which detect the radiation. Then, a section determining step determines the sections of the image space through which the LOR passes, based on the main direction determined in the main direction determining step. A calculation area determining step determines calculation areas in the sections crossed by the LOR, based on the sections determined in the section determining step. The forward projection processing step and back projection processing step carry out the following arithmetic processes more specifically. That is, the forward projection processing step carries out calculations in parallel for every LOR, while the back projection process step carries out calculations in parallel of the forward projection processed data or list data for each of a plurality of areas which are divisions in the calculation area. Thus, the main directions are classified by determining a main direction, to facilitate arithmetic processing of each.

In the data processing method for nuclear medicine of this invention, it is preferred that the above back projection processing step divides the above section into a plurality of areas, makes the plurality of areas divided and dispersed belong to one area, and carries out calculations in parallel for the respective belonging areas. By classifying also the areas in this way, localization in particular threads can be prevented to improve calculating efficiency. Here, the "threads" refer to processing units of parallel data.

In a further preferred example, a plurality of row areas spaced at predetermined intervals are made to belong to the one area. By uniformly dispersing and classifying the areas in this way, localization in particular threads can be prevented with increased effect.

In one example of these data processing methods for nuclear medicine of this invention, use is made of iterative approximation which executes the forward projection processing step and the back projection processing step a plurality of times, for iteratively approximating and updating an image. In the field of nuclear medicine diagnosis, image reconstruction is carried out using iterative approximation as described above. Therefore, iterative approximation may be applied to this invention also. Of course, filtered back projection (FBP) (also called "filtered back projection method") may be applied to the back projection processing step.

A nuclear medicine diagnostic apparatus of this invention comprises a forward projection processing device for obtaining forward projection processed data by carrying out, in parallel for every LOR, forward projection calculations of list data created from event data obtained by detecting radiation; and a back projection processing device for carrying out back projection calculations of the forward projection processed data in parallel for every area divided from a section of image space.

According to the nuclear medicine diagnostic apparatus of this invention, the forward projection processing device obtains forward projection processed data by carrying out, in parallel for every LOR, forward projection calculations of the list data created from the event data obtained by detecting radiation. The back projection processing device carries out back projection calculations of the forward projection processed data or the list data in parallel for every area divided from sections of the image space. Thus, high versatility and an improvement in the speed of calculations can be attained, as with the data processing method for nuclear medicine.

Effects of the Invention

With the data processing method for nuclear medicine and the nuclear medicine diagnostic apparatus according to this invention, forward projection processed data is obtained by carrying out, in parallel for every LOR, forward projection calculations of the list data created from the event data obtained by detecting radiation, and back projection calculations are carried out on the forward projection processed data or the list data in parallel for every area divided from sections of the image space. Thus, high versatility and an improvement in the speed of calculations can be attained.

DESCRIPTION OF REFERENCES

Figure 1:
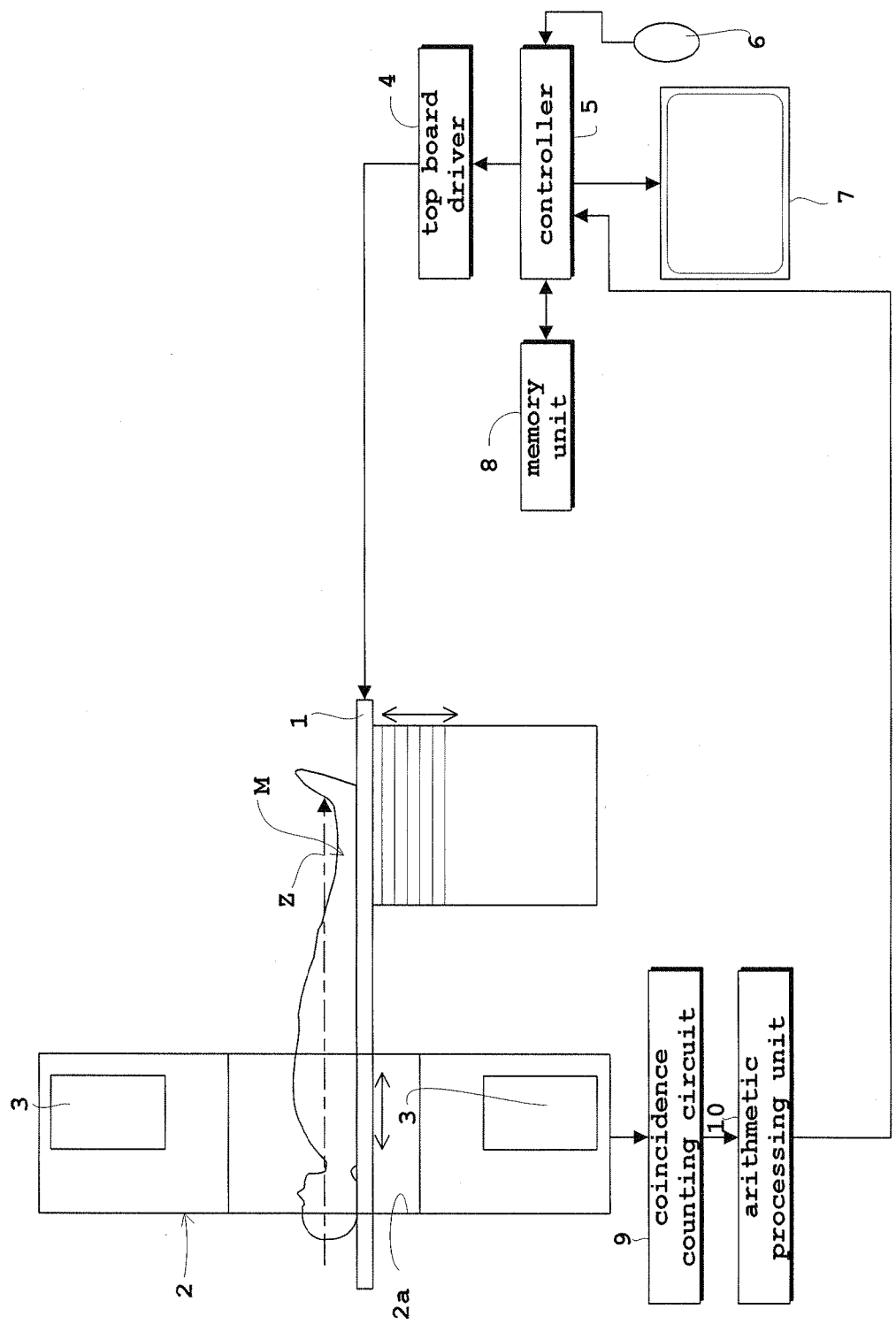
FIG. 1 is a side view and block diagram of a PET (Positron Emission Tomography) apparatus according to an embodiment.
Figure 2:
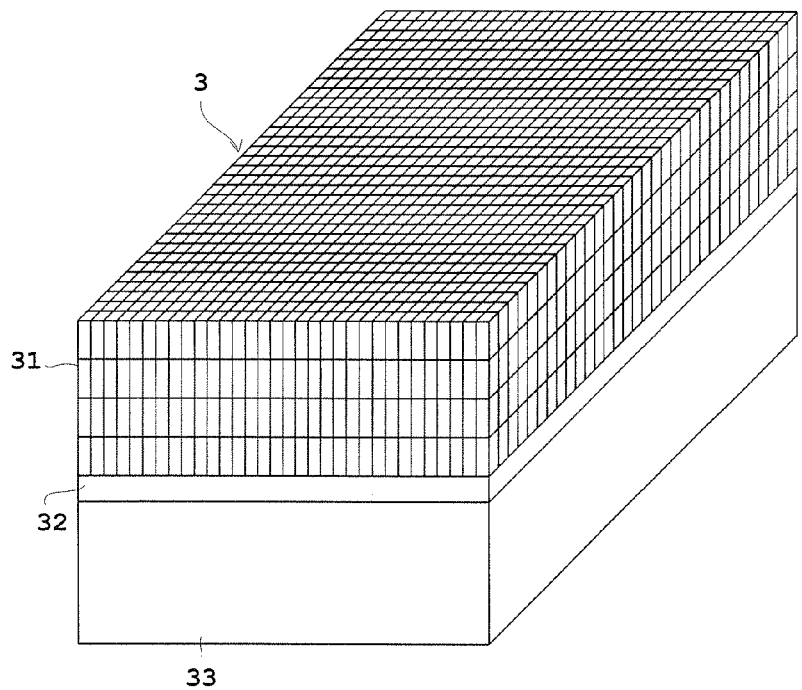
FIG. 2 is an outline perspective view of a gamma-ray detector.

3 . . . gamma-ray detectors
10 . . . arithmetic processing unit
d . . . (directional) vector
M . . . patient Embodiment An embodiment of this invention will be described hereinafter with reference to the drawings. FIG. 1 is a side view and block diagram of a PET (Positron Emission Tomography) apparatus according to the embodiment. FIG. 2 is an outline perspective view of a gamma-ray detector.

The PET apparatus according to this embodiment, as shown in FIG. 1, includes a top board 1 for supporting a patient M. This top board 1 is constructed vertically movable up and down, and movable parallel to the body axis Z of the patient M. With such construction, the patient M placed on the top board 1 is passed through an opening 2a of a gantry 2 to be described hereinafter, and is scanned sequentially from the head to the abdomen and the feet, thereby obtaining images of the patient M. There is no specific limitation as to the sites to be scanned or the order in which the sites are scanned.

Besides the top board 1, the PET apparatus according to this embodiment includes the gantry 2 with the opening 2a, and gamma-ray detectors 3. The gamma-ray detectors 3 are arranged in a ring form so as to surround the body axis Z of the patient M, and are embedded in the gantry 2. The gamma-ray detectors 3 correspond to the detectors in this invention.

In addition, the PET apparatus according to this embodiment includes a top board driver 4, a controller 5, an input unit 6, an output unit 7, a memory unit 8, a coincidence counting circuit 9 and an arithmetic processing unit 10. The top board driver 4 is a mechanism for driving the top board 1 to make the movements described above, and has a motor and the like not shown. The arithmetic processing unit 10 corresponds to the forward projection processing device and the back projection processing device in this invention.

The controller 5 performs overall control of the components forming the PET apparatus according to this embodiment. The controller 5 and arithmetic processing unit 10 are formed of a central processing unit (CPU) and the like. Especially, in this embodiment, the arithmetic processing unit 10 is formed of an SIMD type mechanism represented by a GPU, for example. Of course, the arithmetic processing units 10 may be a SIMD type mechanism other than the GPU, and is not limited to a particular type as long as parallel calculations are possible.

The input unit 6 feeds data and commands inputted by the operator into the controller 5. The input unit 6 is formed of pointing devices represented by a mouse, a keyboard, joystick, trackball, touch panel and so on. The output unit 7 is formed of a display unit represented by a monitor, a printer and the like.

The memory unit 8 is formed of storage media represented by a ROM (Read-only Memory), RAM (Random-Access Memory) and so on. In this embodiment, data relating to coincidence counting such as values of coincidence counting (counts) given by the coincidence counting circuit 9, detector pairs each consisting of two gamma-ray detectors 3 having counted coincidences, and LORs, and various data resulting from arithmetic processing by the arithmetic processing unit 10, are written to and stored in the RAM and are read from the RAM as necessary. The ROM stores beforehand programs for imaging, including various types of nuclear medicine diagnosis, for example. The programs are executed by the controller 5 and arithmetic processing unit 10 to carries out nuclear medicine diagnoses corresponding to the programs, respectively. In this embodiment, in particular, in order to cause a parallel computing architecture called "CUDA (provided by NVIDIA Corp.)" to perform parallel calculations using the GPU, programs relating to CUDA are stored beforehand in the ROM, and processes in steps S1-S5 to be described hereinafter are executed by the arithmetic processing unit 10 executing the programs relating to CUDA.

A scintillator block 31 (see FIG. 2) of each gamma-ray detector 3 converts into light a gamma ray generating from the patient M medicated with a radioactive drug. A photomultiplier tube (PMT) 33 (see FIG. 2) of gamma-ray detector 3 multiplies the converted light and converts it into an electric signal. The electric signal is inputted as an event to the coincidence counting circuit 9.

Specifically, when the patient M is medicated with the radioactive drug, two gamma rays will be generated by annihilation of a positron of a positron-emitting RI. The coincidence counting circuit 9 checks positions of the scintillator blocks 31 (see FIG. 2) and incidence timing of the gamma rays, and determines the inputted event to be proper data only when the gamma rays impinge on two scintillator blocks 31 at opposite sides of the patient M at the same time. When a gamma ray impinges on only one scintillator block 31, the coincidence counting circuit 9 discards it. That is, the coincidence counting circuit 9 detects, based on the above electric signals, that gamma rays are observed simultaneously by two gamma-ray detectors 3.

Events inputted to the coincidence counting circuit 9 are inputted to the arithmetic processing unit 10. The arithmetic processing unit 10 carries out image reconstruction by forward projection process and back projection process, and obtains images of the patient M. The images are sent to the output unit 7 through the controller 5. Thus, a nuclear medicine diagnosis is carried out based on the images obtained by the arithmetic processing unit 10. Specific functions of the arithmetic processing unit 10 will be described hereinafter.

The gamma-ray detector 3, as shown in FIG. 2, has a scintillator block 31, a light guide 32 optically coupled to the scintillator block 31, and a photomultiplier tube (hereinafter abbreviated simply as "PMT") 33 optically coupled to the light guide 32. Each scintillator element forming the scintillator block 31 converts a gamma ray into light by emitting light in response to incidence of the gamma ray. The scintillator element detects the gamma ray through this conversion. The light emitted from the scintillator element is fully diffused in the scintillator block 31, and inputted to the PMT 33 through the light guide 32. The PMT 33 multiplies the light converted by the scintillator block 31, and converts it into an electric signal. The electric signal is sent as an event into the coincidence counting circuit 9 (see FIG. 1) as described above.

Figure 3:
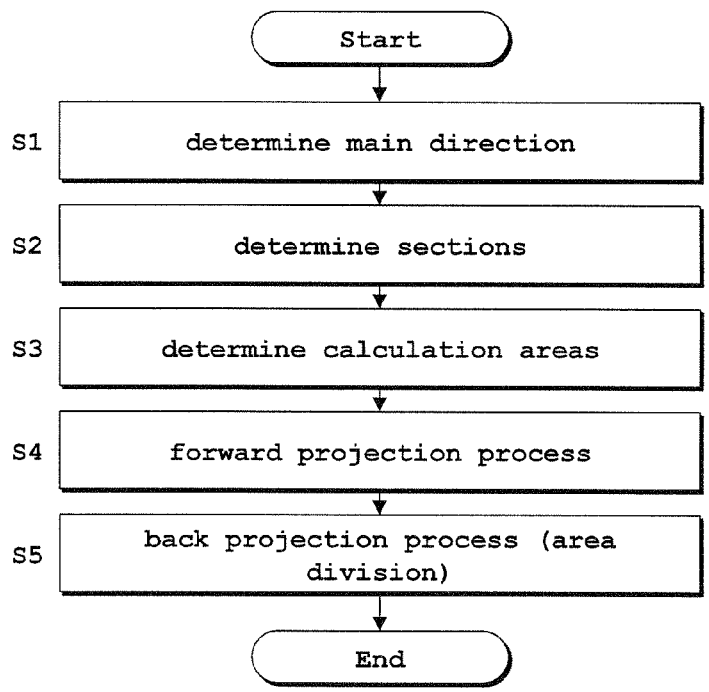
FIG. 3 is a flow chart showing a flow of a method of processing a series of list data.
Figure 4:
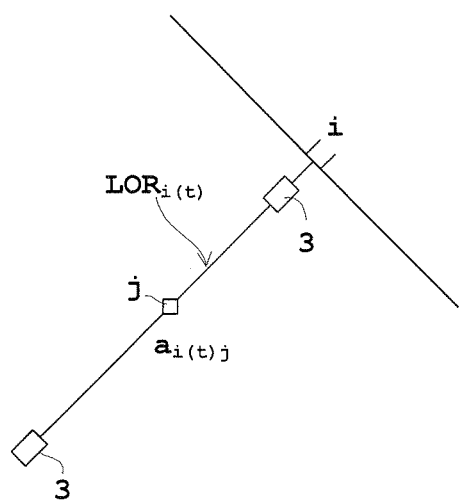
FIG. 4 is a schematic view showing coincidence counting in gamma-ray detectors for illustrating detection probabilities.
Figure 5:
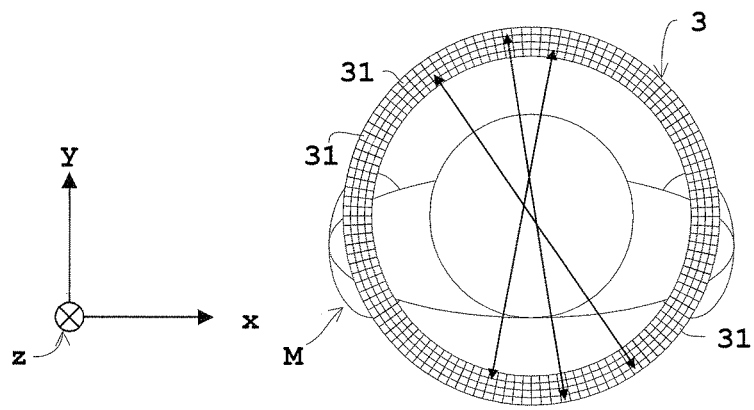
FIG. 5 is a schematic view defining a relationship between an arrangement of gamma-ray detectors arranged in a ring form and 3D coordinates.
Figure 6:
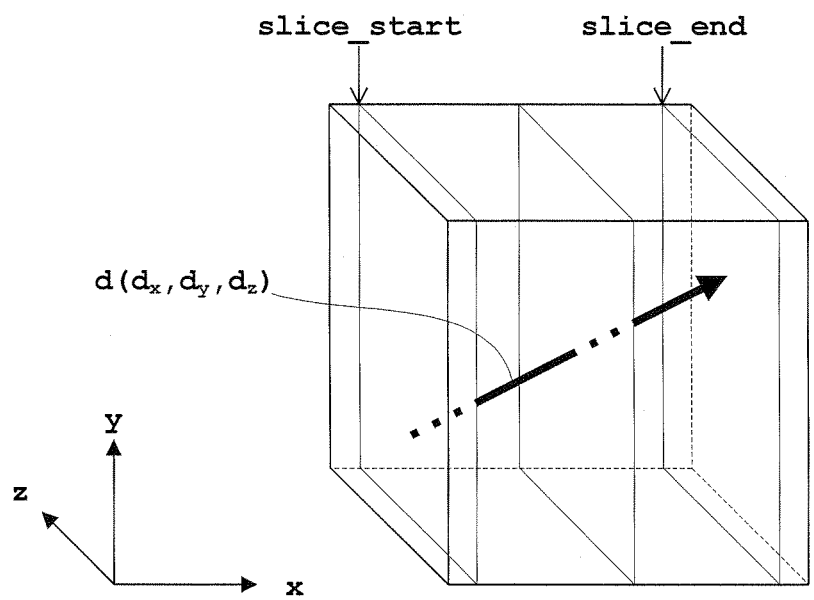
FIG. 6 is a schematic view showing a directional vector of an LOR put on a conceptual diagram of projection.
Figure 7:
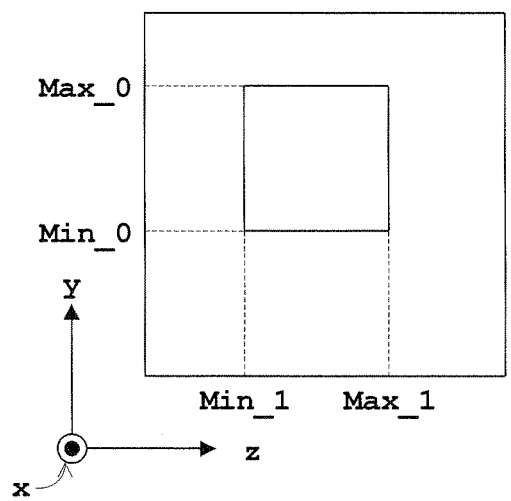
FIG. 7 is a schematic view of a calculation area in a section of image space through which the LOR passes.
Figure 8:
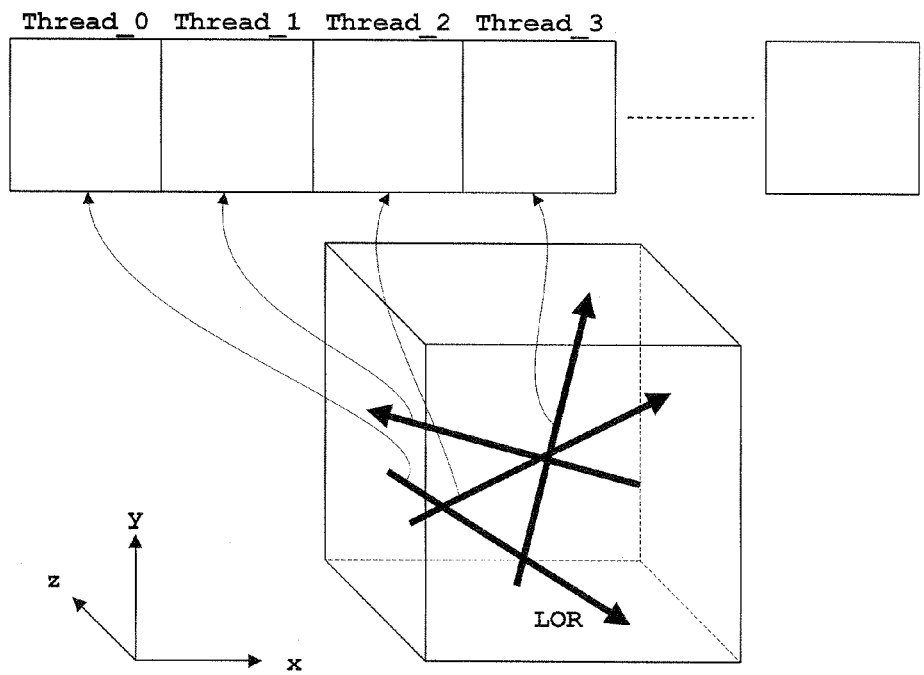
FIG. 8 is a schematic view illustrating parallel calculations of projection values for LORs and one subset.
Figure 9:
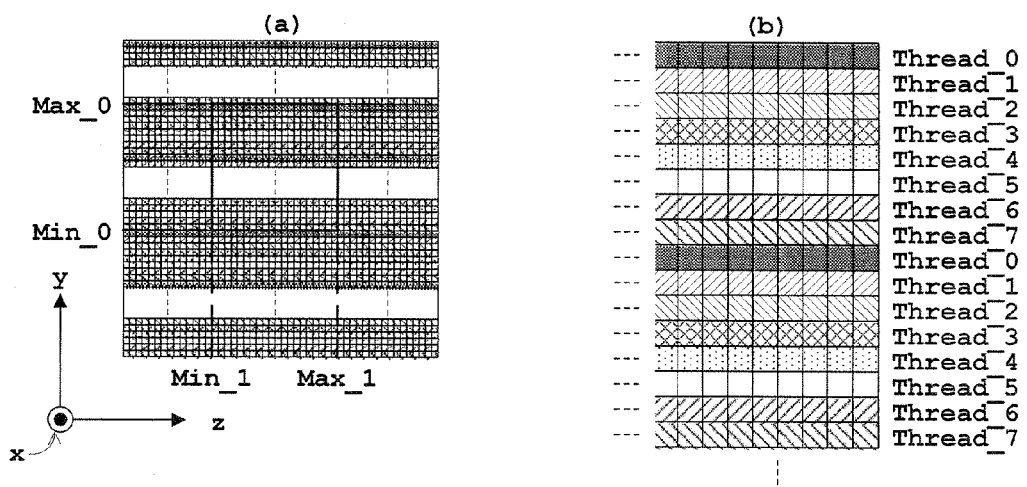
FIG. 9(a) is a schematic view showing divisions of the calculation area in the section of image space through which an LOR passes, and (b) is an enlarged view of (a)
Figure 10:
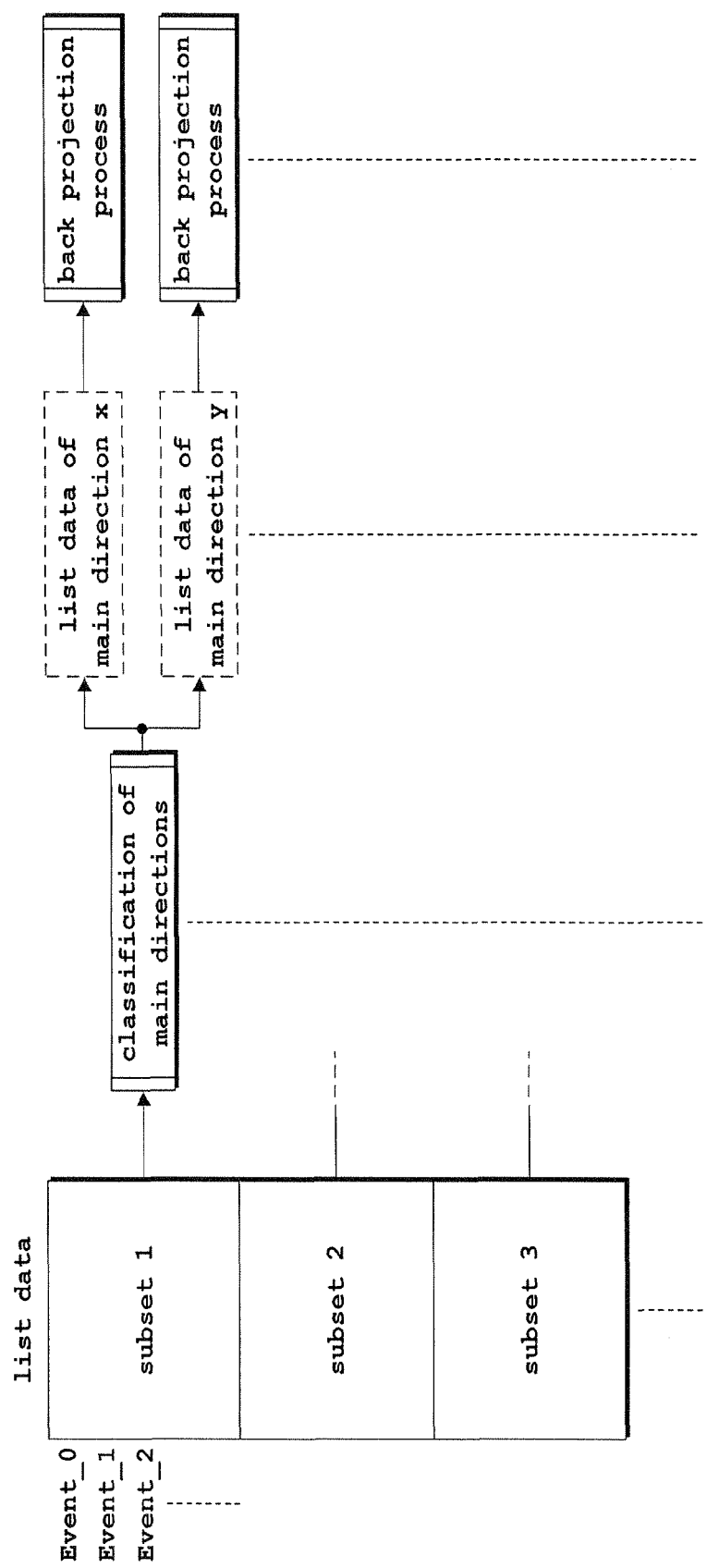
FIG. 10 is a schematic view showing a flow of list data in a series of steps S1-S5.

Next, specific functions of the arithmetic processing unit 10 will be described with reference to FIGS. 3-10. FIG. 3 is a flow chart showing a flow of a method of processing a series of list data. FIG. 4 is a schematic view showing coincidence counting in gamma-ray detectors for illustrating detection probabilities. FIG. 5 is a schematic view defining a relationship between an arrangement of gamma-ray detectors arranged in a ring form and 3D coordinates. FIG. 6 is a schematic view showing a directional vector of an LOR put on a conceptual diagram of projection. FIG. 7 is a schematic view of a calculation area in a section of image space through which the LOR passes. FIG. 8 is a schematic view illustrating parallel calculations of projection values for one subset. FIG. 9 is a schematic view showing divisions of the calculation area in the section of image space through which an LOR passes. FIG. 10 is a schematic view showing a flow of list data in a series of steps S1-S5. FIGS. 4 and 5 show only the scintillator blocks 31 as gamma-ray detectors 3, with the light guides 32 and PMTs 33 omitted. In this embodiment, pixels formed of 3D voxels will be described by way of example.

This embodiment employs list-mode 3D-DRAMA (Dynamic Row-Action Maximum Likelihood Algorithm) using list data as iterative approximation algorithm, and implements parallel calculations using the GPU by means of CUDA noted hereinbefore, after adopting corrections such as attenuation correction, sensitivity correction and random correction. An updating expression of the list-mode 3D-DRAMA is represented by the following expression (1):

[Math 1]

$$x_j^{(k,l+1)} = x_j^{(k,l)} + \lambda^{(k,l)} \cdot \frac{x_j^{(k,l)}}{C_j} \cdot \underbrace{\sum_{t \in S_l} a'_{i(t)j} \cdot \left( \underbrace{\frac{1}{\sum_{j'=0}^{J-1} a'_{i(t)j'} x_{j'}^{(k,l)} + r_i} - p_{lj}}_{FP} \right)}_{BP} \quad (1)$$

$$x_j^{(k+1,0)} = x_j^{(k,L-1)}$$

$$C_j = \max \sum_{t \in S_l} a'_{i(t)j} p_{lj}$$

$$p_{lj} = \sum_{i=0}^{I-1} \mu_i a_{ij} \Big/ \sum_{l'=0}^{L-1} \sum_{t \in S_l} a'_{i(t)j}$$

$$\lambda^{(k,l)} = \frac{\beta_0}{(\beta_0 + l + \gamma k l)}$$

In the above expression (1), i(t) represents a t-th coincidence counting event. A total number of events is divided by the number L of subsets, and each subset is expressed as $S_l$ (l=0, 1, . . . , L−1) (l being the small letter of L). k (k=0, 1, . . . ) is the number of times of iterative approximation, l (the small letter of L) is the number of subsets, and $x_j^{(k,l)}$ is the pixel value of updated voxel j (j=0, 1, . . . , J−1). As shown in FIG. 4, $a_{i(t)j}$ is a probability of gamma ray photons released from voxel j being detected by $LOR_{i(t)}$, and is also called "system matrix". Calculations of the system matrix take also the detector response function into consideration. $C_j$ denotes a normalized matrix, and $p_{lj}$ a blocking factor.

Regarding the blocking factor, Nonpatent Document 2 noted hereinbefore has introduced two types. The present study employs a technique which has a high degree of convergence and which does calculations using all list data. $\lambda^{(k,l)}$ is a relaxation coefficient which is relevant to convergence speed. γ and $\beta_0$ are parameters which control $\lambda^{(k,l)}$. $a'_{i(t)j}$ is $a_{i(t)j}$ after the attenuation correction, and a correction-related definition is shown in the following expression (2):

[Math 2]

$$a'_{i(t)j} = A_{i(t)} a_{i(t)j}$$

$$A_{i(t)} = \exp(-\Sigma \mu_j)$$

$$r_i = 2\tau s_{i(t)0} s_{i(t)1} \quad (2)$$

In the above expression (2), $A_{i(t)j}$ represents an attenuation correction coefficient, and $\mu_j$ represents a distribution of attenuation coefficients. $r_i$ is a value of a random counting rate predicted from count rates $s_{i0}$, $s_{i1}$ of single counting and time window 2τ of coincidence counting.

FP in the above expression (1) represents Forward Projection, and calculations in the forward projection process are carried out in the portion of the above expression (1). On the other hand, BP in the above expression (1) represents Back Projection, and calculations in the back projection process are carried out in the portion of the above expression (1).

First, an initial image $x_j^{(0,0)}$ is set appropriately. The initial image $x_j^{(0,0)}$ may be any image that has a uniform pixel value, with $x_j^{(0,0)} > 0$, for example. The set initial image $x_j^{(0,0)}$ and $a'_{i(t)j}$ corrected by the above expression (2) are repeatedly substituted into the above expression (1), thereby to obtain $x_j^{(0,0)}, \ldots, x_j^{(0,L-1)}$ successively. Finally obtained $x_j^{(0,L-1)}$ is made $x_j^{(1,0)}$ by moving it up to $x_j^{(1,0)}$. Subsequently, $x_j$ is likewise moved up in order ($x_j^{(0,0)}, x_j^{(1,0)} \ldots, x_j^{(k,0)}$). There is no limitation as to the number of times of k representing iteration, but may be set as appropriate. By arranging $x_j$ finally obtained in this way for voxels $v_j$ corresponding thereto, image reconstruction is carried out based on the forward projection process and back projection process, to obtain an image of the patient M.

Specific parallel calculations in each of the forward projection process and back projection process will be described in detail hereinafter.

(Step S1) Determine Main Direction

As shown in FIG. 5, the horizontal axis is set to x, the vertical axis to y, and the body axis of the patient M to z. When the gamma-ray detectors 3 arranged in the ring form are arranged on xy plane, the body axis z becomes an axis extending in the depth direction. As shown in FIG. 6, the direction vector parallel to the LOR is defined as d ($d_x$, $d_y$, $d_z$) (where ∥d∥=1, unit vector), and a main direction of the LOR is determined based on the vector d of the LOR and the direction of arrangement of the gamma-ray detectors 3. Since the gamma-ray detectors 3 are arranged on xy plane, the magnitudes of $d_x$ and $d_y$ of vector d ($d_x$, $d_y$, $d_z$) are compared and the greater is set to the main direction. FIG. 6 is a schematic view when x-direction is made the main direction. This step S1 corresponds to the step of determining a main direction in this invention.

(Step S2) Determine Sections

Sections of image space through which the LOR passes are determined based on the main direction determined in step S1. In this embodiment, planes intersected at right angles by the main direction are determined to be sections of image space through which the LOR passes. Since FIG. 6 is a view where x-direction is made the main direction, the sections are yz planes as shown in FIGS. 6 and 7. This step S2 corresponds to the step of determining sections in this invention.

(Step S3) Determine Calculation Areas

Based on the sections (yz planes in FIG. 6) determined in step S2, calculation areas in the sections crossed by the LOR are determined. First, a section serving as the starting point of the LOR (indicated "slice_start" in FIG. 6) and a section serving as the terminal point of the LOR (indicated "slice_end" in FIG. 6) are determined, and coordinates on the section specifying the starting point and coordinates on the section specifying the terminal point are determined. In FIGS. 6 and 7, since the sections are yz planes, the coordinates on the section specifying the starting point are y, z coordinates, and similarly the coordinates on the section specifying the terminal point are y, z coordinates. Since the vector extends in one direction, one of the y coordinates of the starting point and terminal point is a minimum coordinate (indicated "Min_0" in FIG. 7), and the other is a maximum coordinate (indicated "Max_0" in FIG. 7). Similarly, one of the z coordinates of the starting point and terminal point is a minimum coordinate (indicated "Min_1" in FIG. 7), and the other is a maximum coordinate (indicated "Max_1" in FIG. 7). That is, on the sections, the LOR will cross a maximum coordinate position from a minimum coordinate position on the respective sections. Therefore, the calculation area crossed by the LOR is an area marked out by Min_0, Max_0, Min_1 and Max_1 as shown in FIG. 7. This step S3 corresponds to the step of determining calculation areas in this invention.

(Step S4) Forward Projection Process

An arithmetic process is carried out in parallel on list data in the calculation areas determined in step S3. Specifically, a system matrix is obtained for each voxel j, and in the range of the determined calculation area, a projection value is updated by multiplying the portion indicated FP in equation (1) noted hereinbefore by the pixel value, followed by addition. The parallel calculations with equation (1) noted hereinbefore are carried out for each LOR. Regarding the memory for substituting the projection value, it is arranged for writing one element per event, per subset, which is written as shown in FIG. 8, for example. "Thread_0", "Thread_1", "Thread_2", "Thread_3", . . . in FIG. 8 show processing units of parallel data written. Each LOR is in a one-to-one relationship to each thread per subset.

When, for example, 3276800 events in total are processed and the number of subsets is 128, the number of events is 25600 (=3276800/128) per subset. Therefore, since calculations are carried out for 25600 events in 25600 threads when performing parallel calculations in the forward projection process, places where the projection values are written differ from thread to thread, which does not give rise to a competition for memory. This step S4 corresponds to the forward projection processing step in this invention.

(Step S5) Back Projection Process (Area Division)

The back projection process is carried out on the forward projection processed data or list data resulting from the forward projection process in step S4. In this case, each section of the image space through which a LOR passes is divided into a plurality of areas, the plurality of areas divided and dispersed are made to belong to one area, and calculations are carried out in parallel for the respective belonging areas. Specifically, for each belonging area, a back projection value is updated by addition in the portion indicated BP in equation (1) noted hereinbefore.

To describe this in more detail with reference to FIG. 9, row areas at predetermined intervals are made to belong to one area. When, for example, the calculation area is a section (slice) of 256×256 pixels, assuming that rows at intervals of 31 rows are defined as one area, each slice will be divided into 32 areas, and eight (=256/32) rows will make up one area. In this case, therefore, row areas at intervals of 31 rows are made to belong to one area. In the case of FIG. 9, for convenience of illustration, the rows spaced apart by seven rows are defined as one area. FIG. 9(b) is an enlargement of FIG. 9(a). As shown in FIG. 9, with the rows spaced apart by seven rows being defined as one area, each slice is divided into eight areas. That is, each is divided into areas indicated "Thread_0", "Thread_1", . . . "Thread_7" in FIG. 9(b). This step S5 corresponds to the back projection processing step in this invention.

A list data flow in the series of steps S1-S5 is as shown in FIG. 10. That is, with the main direction determined in step S1, the list data (indicated "Event_0", "Event_1", "Event_2", . . . in FIG. 10) of each event (i.e. each LOR) is classified by the main direction. Since the magnitudes of $d_x$ and $d_y$ are compared and the greater is made the main direction in this embodiment, classification is made as list data whose main direction is x-direction (indicated "list data of main direction x in FIG. 10) and list data whose main direction is y-direction (indicated "list data of main direction y in FIG. 10), and each is put to arithmetic processing in parallel in the back projection process in step S5.

The iterative approximation noted hereinbefore is not limited to the DRAMA noted hereinbefore, but may be static RAMLA (Row-Action Maximum Likelihood Algorithm), may be ML-EM (Maximum Likelihood Expectation Maximization), or may be OSEM (Ordered Subset ML-EM).

According to the PET apparatus and the processing method in this embodiment having the construction described above, step S4 (forward projection process) obtains forward projection processed data by carrying out, in parallel for every LOR, forward projection calculations of the list data created from the event data obtained by detecting gamma rays. Step S5 (back projection process) carries out the back projection calculations of the forward projection processed data or the list data in parallel for every area divided from sections of the image space. Since the arithmetic process is carried out in parallel on the list data for every LOR, the forward projection calculations and back projection calculations can be realized without using the mechanism peculiar to the GPU, for example, which can be applied to other arithmetic mechanisms and have versatility. Since parallel processing is carried out on the list data and the parallel processing is carried out through the forward projection calculations and back projection calculations, respectively, a competition for memory can be prevented to realize an improvement in speed. In the back projection calculations, as distinct from the forward projection calculations, a competition for memory may take place. In order to prevent this, step S5 (back projection process) carries out the back projection calculations in parallel for every area divided from sections of the image space. As a result, high versatility and an improvement in the speed of calculations can be attained.

Since the main directions of the LORs are located at random, it is preferable in this embodiment to classify the main directions first. That is, step S1 (determine main direction), preferably, determines the main direction of an LOR based on vector d of the LOR and the direction of arrangement of gamma-ray detectors 3 which detect gamma rays. And based on the main direction determined in step S1 (determine main direction), step S2 (determine sections) determines sections of the image space through which the LOR passes. Based on the sections determined in step S2 (determine sections), step S3 (determine calculation areas) determines calculation areas in the sections crossed by the LOR. Step S4 (forward projection process) and step S5 (back projection process) carry out the foregoing arithmetic processes more specifically. That is, step S4 (forward projection process) carries out calculations in parallel for every LOR, while step S5 (back projection process) carries out calculations in parallel of the forward projection processed data or list data for each of a plurality of areas which are divisions in the calculation area. Thus, the main directions are classified by determining a main direction, to facilitate arithmetic processing of each.

In this embodiment, step S5 (back projection process) described hereinbefore, preferably, divides the section described hereinbefore into a plurality of areas, makes the plurality of areas divided and dispersed belong to one area, and carries out calculations in parallel for the respective belonging areas. By classifying also the areas in this way, localization in particular threads can be prevented to improve calculating efficiency.

More preferably, respective row areas at predetermined intervals are made to belong to one area (see FIG. 9). By uniformly dispersing and classifying the areas in this way, localization in particular threads can be prevented with increased effect.

In this embodiment, application is made to iterative approximation which executes the foregoing step S4 (forward projection process) and step S5 (back projection process) a plurality of times, for iteratively approximating and updating the image. That is, the above arithmetic process is carried out in parallel using iterative approximation. In the field of nuclear medicine diagnosis, image reconstruction is carried out using iterative approximation as described above.

The PET apparatus according to this embodiment includes the arithmetic processing unit 10 for carrying out the arithmetic process in steps S1-S5 described above which obtain the forward projection processed data by putting the list data created from the event data obtained by detecting gamma, to the forward projection calculations in parallel for the respective LORs, and carrying out the back projection calculations of the forward projection processed data in parallel for every area divided from the sections of image space. By, applying the method of steps S1-S5 in this embodiment to the PET apparatus, high versatility and an improvement in the speed of calculations can be attained, as in the case of the method of steps S1-S5 in this embodiment.

In this embodiment, CUDA implementation of the list-mode 3D-DRAMA noted hereinbefore has been adopted, and a review has been made of improvement in the speed of image reconstruction. It has been confirmed as a result that an improvement in speed of about 18 times is realized in relation to list data of 3.2M events. It has also been confirmed that reconstructed images produced through calculations using the GPU are substantially the same as in the case of using a general CPU.

This invention is not limited to the foregoing embodiment, but may be modified as follows:

(1) In the foregoing embodiment, the above arithmetic processes are carried out in parallel using iterative approximation in step S4 (forward projection process) and step S5 (back projection process) described above. Instead, Feld-kamp method using filtered back projection may be applied to the back projection processing step.

(2) In the foregoing embodiment, the main directions are classified by determining a main direction, but it is not absolutely necessary to determine the main direction. However, in order to facilitate each arithmetic process, it is preferable to classify the main directions by determining a main direction as in the embodiment.

(3) In the foregoing embodiment, a main direction is determined after setting the horizontal axis to x, the vertical axis to y and the body axis of the patient M to z, but the invention is not limited to these directions of axes.

(4) In the foregoing embodiment, a main direction is determined after arranging in xy plane the gamma-ray detectors 3 arranged in a ring form as shown in FIG. 5. However, the main direction may be determined as appropriate according to an arranged state of the gamma-ray detectors. In the case of detectors in a non-ring form, a main direction may be determined based on a plane on two detectors used for coincidence counting.

(5) In the foregoing embodiment, when determining a main direction, the greater one is made the main direction, but this is not necessarily limitative. If a main direction is determined based on a fixed rule, the smaller one may be made the main direction, for example.

(6) In the foregoing embodiment, planes to which the main direction extends perpendicular are determined to be sections of the image space through which an LOR passes. It is not absolutely necessary to determine the planes to which the main direction extends perpendicular to be such sections. Planes crossed at angles other than 90° may be determined to be such sections.

(7) In the foregoing embodiment, respective row areas at predetermined intervals are made to belong to one area. Instead, divisions may be block areas other than the row areas, and a number of these may be collected together to belong to one area.

(9) In the foregoing embodiment, the nuclear medicine diagnostic apparatus has been described. However, the invention is applicable also to a gamma camera with a collimator mechanism, and to SPECT.

The invention claimed is:

1. A data processing method for nuclear medicine comprising:
   a forward projection processing step for obtaining forward projection processed data by carrying out, in parallel for every LOR, forward projection calculations of list data created from event data obtained by detecting radiation; and
   a back projection processing step for carrying out back projection calculations of the forward projection processed data or the list data, wherein an image space comprises a plurality of sections and each section is divided into a plurality of areas, and wherein the back projection calculations are performed in parallel for every area.

2. The data processing method for nuclear medicine according to claim 1 comprising:
   a main direction determining step for determining a main direction of the LOR based on a vector of the LOR and a direction of arrangement of detectors which detect the radiation;
   a section determining step for determining the sections of the image space through which the LOR passes, based on the main direction determined in the main direction determining step; and a calculation area determining step for determining calculation areas in the sections crossed by the LOR, based on the sections determined in the section determining step;

wherein the forward projection processing step carries out calculations in parallel for every LOR; and the back projection processing step carries out calculations in parallel for a plurality of areas provided by dividing the calculation area.

3. The data processing method for nuclear medicine according to claim 1, wherein the back projection processing step divides the section into a plurality of areas, makes the plurality of areas divided and dispersed belong to one area, and carries out calculations in parallel for the respective belonging areas.

4. The data processing method for nuclear medicine according to claim 3, wherein a plurality of row areas spaced at predetermined intervals are made to belong to the one area.

5. The data processing method for nuclear medicine according to claim 1, wherein use is made of iterative approximation which executes the forward projection processing step and the back projection processing step a plurality of times, for iteratively approximating and updating an image.

6. A nuclear medicine diagnostic apparatus comprising:

a forward projection processing device for obtaining forward projection processed data by carrying out, in parallel for every LOR, forward projection calculations of list data created from event data obtained by detecting radiation; and a back projection processing device for carrying out back projection calculations of the forward projection processed data, wherein an image space comprises a plurality of sections and each section is divided into a plurality of areas, and wherein the back projection calculations are performed in parallel for every area.

7. A data processing method for nuclear medicine comprising:

a back projection processing step for carrying out back projection calculations of the forward projection processed data or the list data, wherein an image space comprises a plurality of sections and each section is divided into a plurality of areas, and wherein the back projection calculations are performed in parallel for every area.

* * * * *